United States Patent [19]

Olesen et al.

[11] Patent Number: Plant 6,261

[45] Date of Patent: Aug. 30, 1988

[54] ROSE PLANT NAMED POULTEX

[76] Inventors: Pernille Olesen; Mogens N. Olesen, both of Hillerodvej 49, DK 3480 Fredensborg, Denmark

[21] Appl. No.: 907,372

[22] Filed: Sep. 15, 1986

[51] Int. Cl.[4] ..... A01H 5/00

[52] U.S. Cl. ..... Plt./8

[58] Field of Search ..... Plt. 8

*Primary Examiner*—Robert E. Bagwill

*Attorney, Agent, or Firm*—Vincent G. Gioia

[57] ABSTRACT

A new miniature rose variety of unusual Buttercup yellow coloring.

1 Drawing Sheet

The present invention relates to a new and distinct variety of rose plant of the miniature rose class, which was originated by my crossing as seed parent the rose known as "Mini-Poul" and as pollen parent an unpatented, unnamed seedling of my creation. The varietal denomination of this new variety is "Poultex".

Among the novel characteristics possessed by this new variety which distinguish it from its parents and all other varieties of which I am aware are its attractive Buttercup yellow colored flowers of good form that maintain their color and form through development and aging. Flowers are relatively large for a miniature and are of a size commonly referred to as a patio rose. Asexual reproduction by budding of the new variety as performed in Fredensborg, Denmark, shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "15A" is plate 15A of The Royal Horticultural Society Colour Chart.

Parentage: Seedling.

*Seed parent.*—"Mini-Poul".

*Pollen parent.*—Unnamed, unpatented seedling.

Class: Miniature.

The following observations are made of specimens grown outdoors in Fredensborg, Denmark, during the month of August.

FLOWER

Blooming habit: Near continuous.

A. Bud:

(1) *Size.*—Large for miniature.

(2) *Form.*—Long, pointed, ovoid.

(3) *Color.*—Before sepals divide, first color is Buttercup yellow, near 15A to B.

(4) *Sepals.*—Longer than bud, simple.

(5) *Peduncle.*—Length — about 40 to 50 mm. Aspect — straight. Strength — erect. Color —green.

B. Bloom:

(1) Size.—Average size when fully expanded — about 50 mm.

(2) *Borne.*—Singly and several together in sprays.

(3) *Form.*—High centered at first, opens slowly, maintains form throughout, edges of outer petals roll under then reflex to points as flowers age.

(4) *Petalage.*—Number of petals under normal conditions — about 20.

(5) *Color.*—After sepals fall and as flower opens, Buttercup yellow color, near 15A to B and 16C, predominates. Edges of outer petals roll under. Yellow coloring is stable and well maintained.

C. Petals:

(1) *Texture.*—Thick, good substance.

(2) *Appearance.*—Inside — velvety, outside — satiny.

(3) *Form.*—Broad, fan shaped with smooth round edge.

(4) *Arrangement.*—Regularly arranged, imbricated.

(5) *Petaloids in center.*—Few.

(6) *Persistence.*—Drop off cleanly.

(7) *Fragrance.*—Slight apple-rose.

(8) *Lasting quality.*—Long on plant and as cut flower.

REPRODUCTIVE ORGANS

A. Stamens, filaments and anthers:

(1) *Arrangement.*—Regularly arranged around styles.

(2) *Color.*—Yellow.

B. Pollen:

*Color.*—Yellow.

C. Styles: Even length, bunched.

D. Stigmas:

*Color.*—Greenish yellow.

E. Hips: Globular, about 15 mm, yellow orange, seeds do not protrude.

PLANT

A. Form: Upright, bushy.

B. Growth: Vigorous, uniform branching.

*Height attained.*—About 40–50 cm.

C. Foliage: Compound 5 leaflets.

(1) *Size.*—Small.

(2) *Quantity.*—Abundant.

(3) *Color.*—New foliage: Upper side — green. Under side — green, dull. Old foliage: Upper side — green, glossy. Under side —green, dull.
(4) *Shape.*—Oval, pointed.
(5) *Texture.*—Upper side is glossy and under side is matte.
(6) *Edge.*—Serrated.
(7) *Serration.*—Serrate.
(8) *Leaf stem.*—Color — Dark green.
(9) *Stipules.*—Medium, broad, pointed.
(10) *Resistance to disease.*—Blackspot — good. Mildew — good. Rust — good.

D. Wood:
(1) *New wood.*—Color — light green. Bark — smooth.
(2) *Old wood.*—Color — dark green. Bark — smooth.

E. Thorns:
(1) *Thorns.*—Quantity (main stalk) — ordinary. On laterals from stalk — few. Form — slightly curved, pointed. Length — short. Color — green. Position — regular.
(2) *Prickles.*—None on main stems, profuse on laterals.

F. Winter hardiness: Winter hardy.

I claim:

1. A new and distinct variety of rose plant of the miniature rose class, substantially as shown and described, characterized particularly by relatively large, unusually attractive, Buttercup yellow colored flowers of good form that hold color well through development and aging.

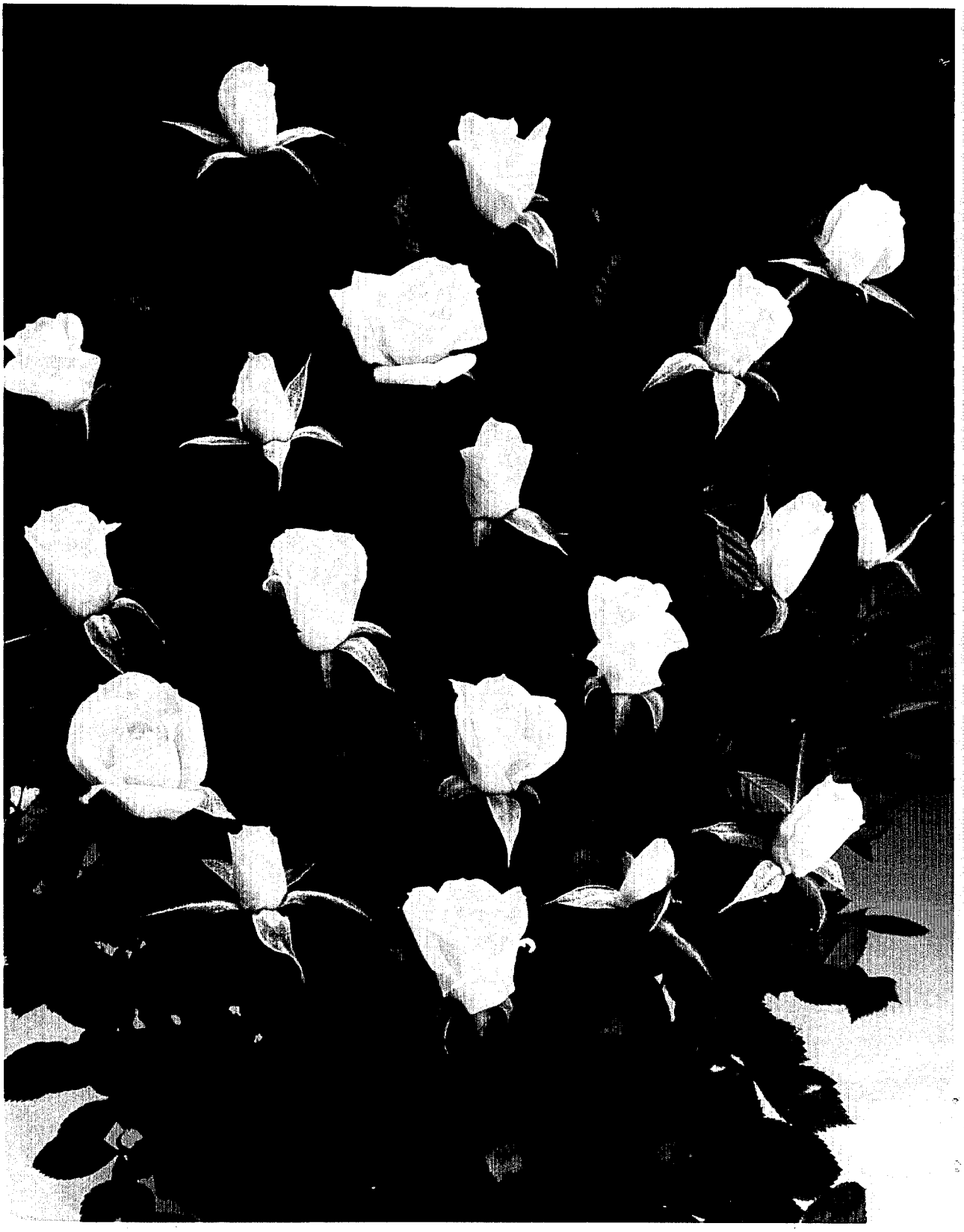

* * * * *